United States Patent [19]
Gildersleeve

[11] Patent Number: 5,316,547
[45] Date of Patent: May 31, 1994

[54] ORTHOPEDIC BRACE HAVING PNEUMATIC PADS

[75] Inventor: Richard E. Gildersleeve, Escondido, Calif.

[73] Assignee: Smith & Nephew Donjoy, Inc., Carlsbad, Calif.

[21] Appl. No.: 907,160

[22] Filed: Jul. 1, 1992

[51] Int. Cl.$^5$ .............................. A61F 5/00
[52] U.S. Cl. ................... 602/26; 602/13; 602/16
[58] Field of Search ............... 602/13, 26, 16, 23, 602/26; 128/112.1, 117.1, 118.1, DIG. 20; 441/60, 88, 122

[56] References Cited

U.S. PATENT DOCUMENTS

| | | | |
|---|---|---|---|
| 2,531,074 | 11/1950 | Miller | 128/DIG. 20 X |
| 3,581,741 | 6/1971 | Rosnan | 602/26 X |
| 3,955,565 | 5/1976 | Johnson, Jr. | |
| 4,201,203 | 5/1980 | Applegate | 602/26 |
| 4,219,892 | 7/1980 | Rigdon | 602/26 X |
| 4,280,489 | 7/1981 | Johnson, Jr. | |
| 4,287,920 | 9/1981 | Johnson, Jr. | |
| 4,567,887 | 2/1986 | Couch, Jr. | 128/118.1 X |
| 4,628,954 | 12/1988 | Johnson, Jr. | |
| 4,667,672 | 5/1987 | Romanowski | 128/DIG. 20 X |
| 4,703,750 | 11/1987 | Sebastian et al. | 602/13 |
| 4,872,448 | 10/1989 | Johnson, Jr. | |
| 4,938,207 | 7/1990 | Vargo | |
| 5,088,478 | 2/1992 | Grim | |
| 5,107,823 | 4/1992 | Fratesi | 602/26 X |
| 5,113,599 | 5/1992 | Cohen et al. | |
| 5,125,400 | 6/1992 | Johnson, Jr. | 602/13 |

FOREIGN PATENT DOCUMENTS 2627381 8/1989 France ...................... 602/16

*Primary Examiner*—Richard J. Apley
*Assistant Examiner*—Linda C. M. Dvorak
*Attorney, Agent, or Firm*—Rodney F. Brown

[57] ABSTRACT

An orthopedic brace is provided having one or more pads mounted thereon to provide secure and comfortable support for the brace when positioned against the body of a user. Each pad includes at least one pneumatic bladder, formed from a flexible skin permanently sealed to enclose a volume of gas therein. In a first embodiment, the brace has a point pad mounted thereon which is configured to conform to a surface of the body overlying a skeletal protrusion. The point pad contains a bladder having a substantially closed-loop configuration circumscribing the skeletal protrusion and having an interior opening to receive the protrusion. In a second embodiment, the brace has an areal pad mounted thereon which is configured to conform to a surface of the body overlying a curved, but relatively level, skeletal structure or soft tissue. The areal pad is a plurality of interconnected gas-inflated chambers that are maintained in fluid isolation from one another by flexible seams positioned between adjacent chambers. Alternatively, the areal pad is a bladder having a plurality of interconnected gas-inflated segments that are in fluid communication with one another via flow channels provided through the flexible seams positioned between adjacent segments. In either case, the flexible seams act as a pivot enabling articulation of the pad.

18 Claims, 3 Drawing Sheets

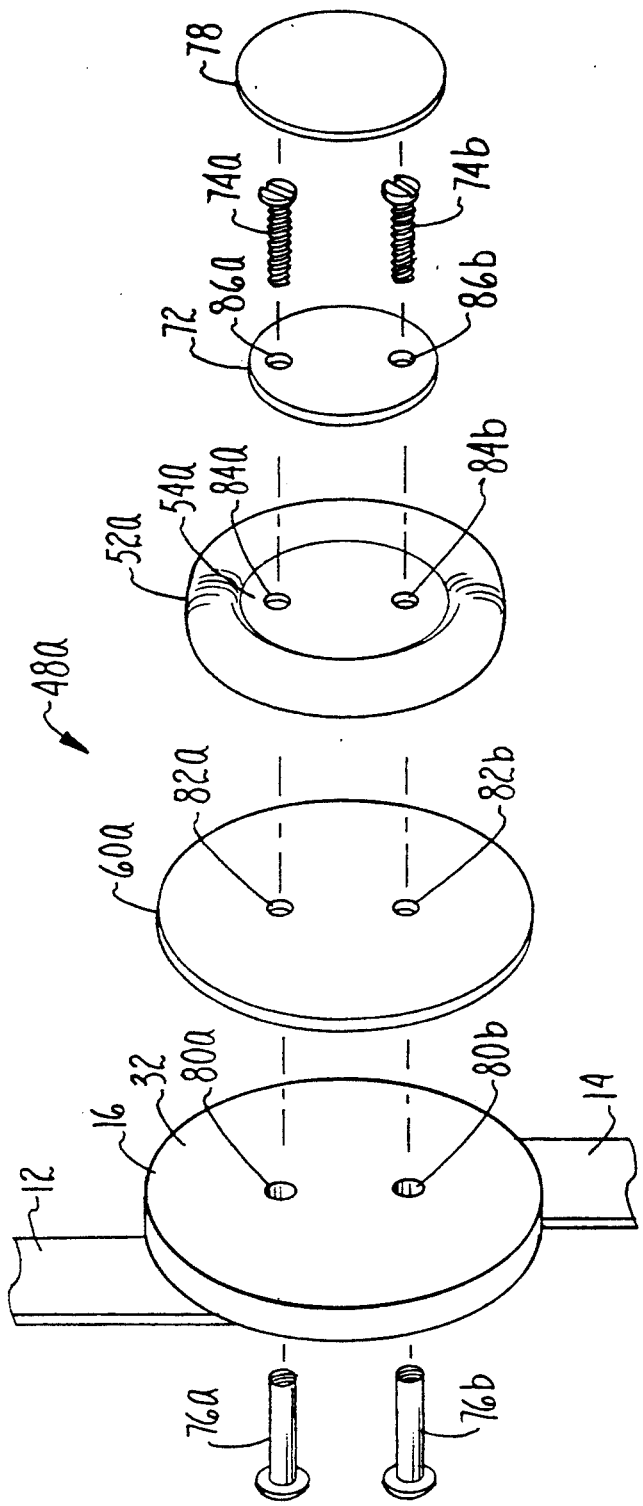
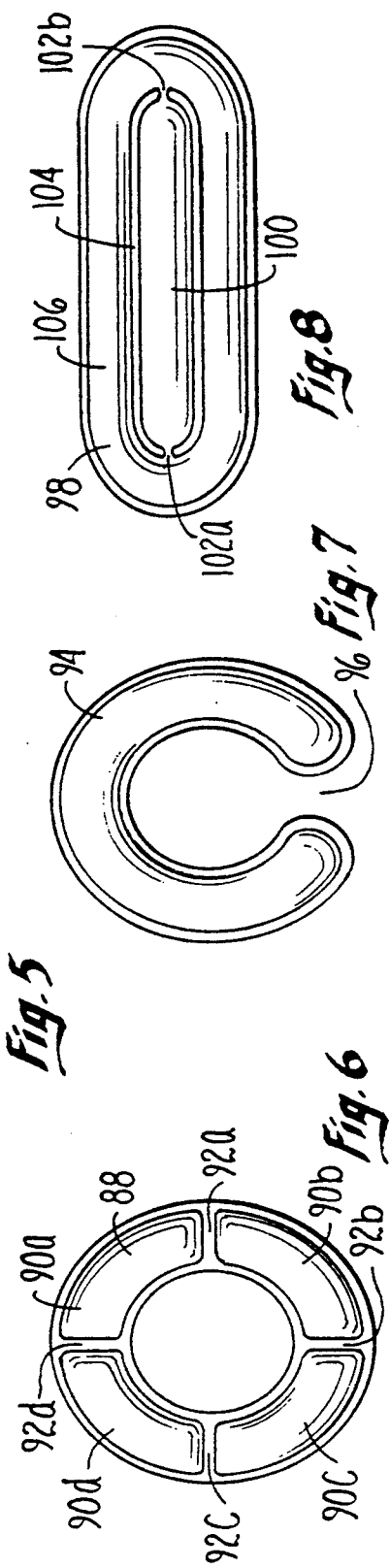

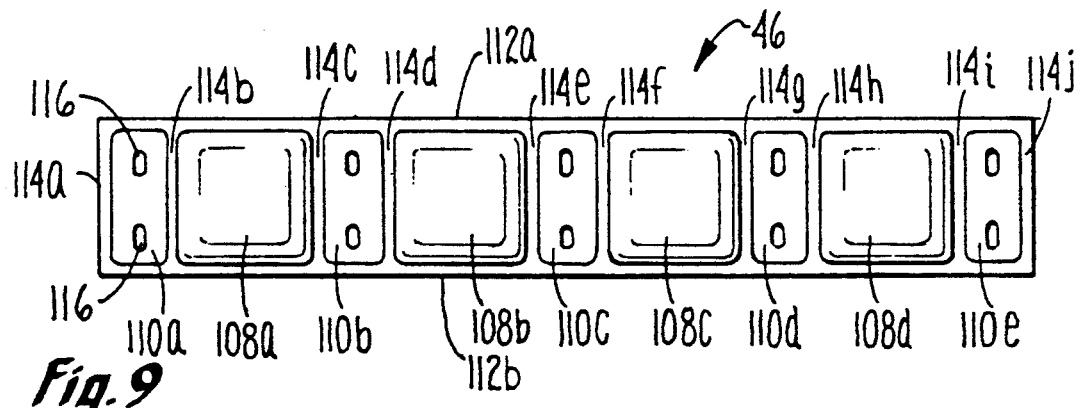
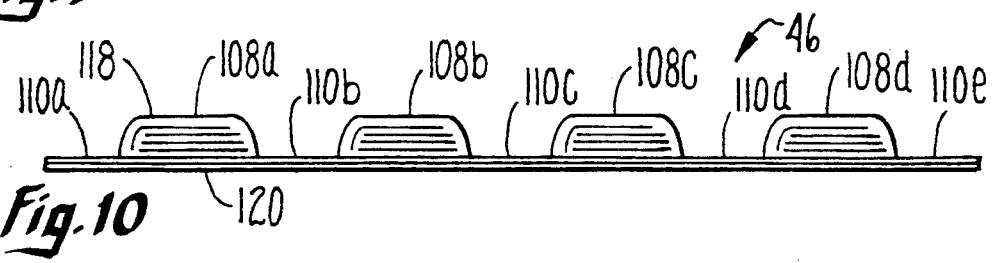
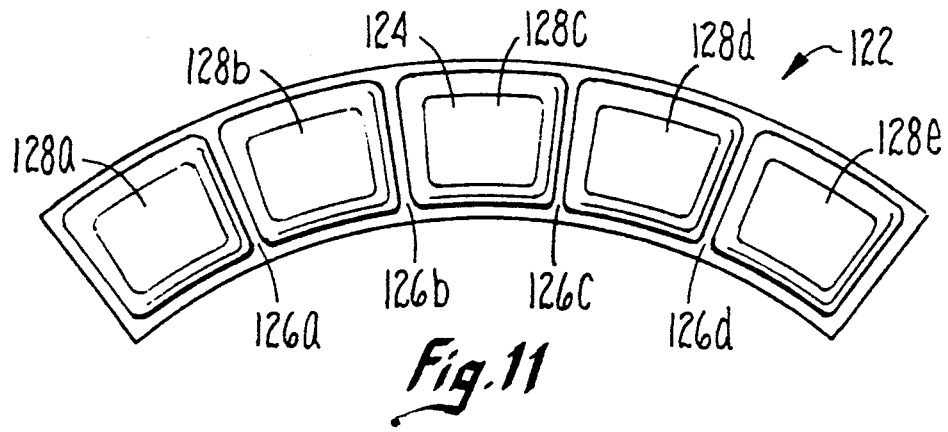
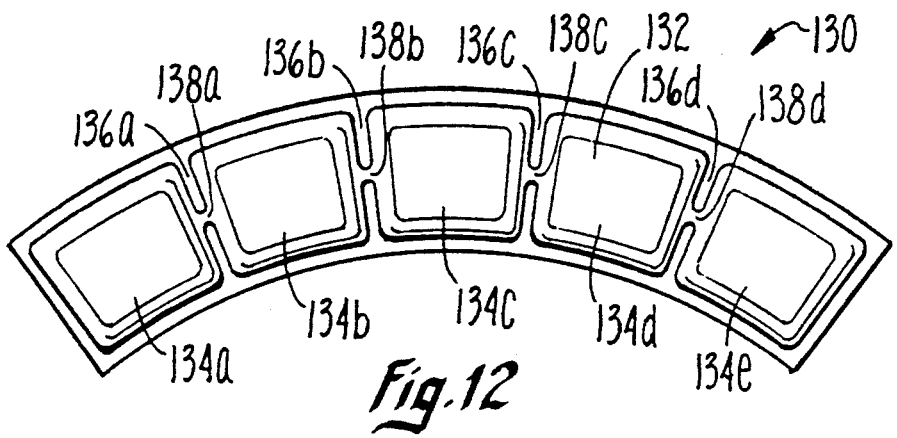

ORTHOPEDIC BRACE HAVING PNEUMATIC PADS

TECHNICAL FIELD

The present invention relates generally to orthopedic braces, and particularly to an orthopedic brace having pads mounted thereon for supporting the brace against the body of a user. More particularly, though not exclusively, the present invention relates to an orthopedic brace having pneumatic pads mounted thereon that support the brace against the body of a user by conforming to the contours of the body.

BACKGROUND OF THE INVENTION

Orthopedic braces are commonly employed on the body of a user to stabilize a skeletal joint that has been weakened by injury or other infirmity. The brace is typically made up of a number of rigid structural components that are dynamically linked together by hinges to support the joint during user activity. The brace is positioned on the body such that the hinges traverse the joint being stabilized, while the rigid components are secured to the body at a plurality of contact points above and below the joint.

Foam pads are often used to cushion the contact points between the body and the rigid components of the brace because of the ability of the foam to conform to the body of the user. Despite the presence of the foam pads, however, the user often experiences discomfort from painful point loads while wearing the brace because of the high compression forces the brace applies to the body across the contact points during physical activity. Conventional foam pads are either overly compressive or overly stiff, diminishing there cushioning effect. Lightweight foams have not been found which are adequately compressive for the comfort of the user, yet which are sufficiently firm to provide a stable base of support for the brace against the body of the user.

Accordingly, it is an object of the present invention to provide an orthopedic brace that can be secured to the body of a user with both a high degree of stable support and a high degree of user comfort. It is further an object of the present invention to provide an orthopedic brace employing lightweight pads that comfortably stabilize the brace against the body of the user by dynamically conforming to and firmly gripping the contours of the body while fully cushioning the contours from the rigid structural components of the brace.

SUMMARY OF THE INVENTION

The present invention is an orthopedic brace having one or more pads mounted thereon which provide secure and comfortable support for the brace when positioned against the body of a user. Each pad comprises at least one pneumatic bladder, formed from a flexible skin shaped into a containment configuration and having a substantially permanent seal to enclose a volume of gas therein.

In a first embodiment, the brace has a point pad mounted thereon which is configured to conform to a surface of the body overlying a skeletal protrusion, such as a condyle, and particularly a knee condyle. As such, point pads can be mounted on the hinges of an orthopedic knee brace, to both cushion and grip the knee. The point pad is a gas-inflated bladder having a substantially closed-loop configuration with an opening interior to the loop. The pad is sized such that the bladder circumscribes the perimeter of the condyle and the interior opening receives the apex of the condyle.

In a second embodiment, the brace has an areal pad mounted thereon which is configured to conform to a surface of the body overlying curved, but relatively level, skeletal structures or soft tissue, such as body surfaces above and below a joint, and particularly the upper and lower leg above and below the knee joint. As such, areal pads can be mounted on the upper and lower leg cuffs of an orthopedic knee brace, to cushion and grip the upper and lower legs above and below the knee, respectively. The areal pad is a plurality of interconnected gas-inflated chambers that are maintained in fluid isolation from one another by flexible seams positioned between adjacent chambers of the pad. Alternatively, the areal pad is a bladder having a plurality of interconnected gas-inflated segments that are in fluid communication with one another via flow channels provided through the flexible seams positioned between adjacent segments. In either case, the flexible seams act as a pivot enabling articulation of the pad.

In either the areal pad or the point pad, the construct of the pad preferably includes two sheets of an elastically deformable film with one overlying the other. The sheets are joined together by at least one seam that defines the configuration of the bladder and seals the bladder off from the external environment. The pad may further be provided with a thickened elastic backing that is attached to one of the sheets as a cushion between the sheet and the rigid structural components of the brace. The backing is attached to the inside face of any desired brace component with the bladder engaging the adjacent body surface of the user.

The orthopedic brace of the present invention is further provided with a fastener for attaching the pad to a rigid brace component. Any number of conventional fasteners can be used for this purpose including screws, rivets, and the like. A preferred fastener, however, is a hook and loop fastener. A strip of hooks are affixed to the pad and a strip of loops are affixed to the rigid brace component, or vice versa, at the desired point of attachment. The hook and loop fastener provides secure, yet removable, attachment of the pad to the brace component.

The present invention will be further understood, both as to its structure and operation, from the accompanying drawings, taken in conjunction with the accompanying description, in which similar reference characters refer to similar parts.

BRIEF DESCRIPTION OF THE DRAWINGS

FIG. 5 is an exploded perspective view of the point pad shown in FIG. 3 having an alternate fastener.

FIG. 6 is a frontal view of a primary bladder for use on a point pad associated with the knee brace of FIG. 2.

FIG. 7 is a frontal view of another embodiment of a primary bladder for use on a point pad associated with the knee brace of FIG. 2.

FIG. 8 is a frontal view of yet another embodiment of a primary bladder for use on a point pad associated with the knee brace of FIG. 2.

FIG. 9 is a frontal view of an areal pad associated with the knee brace of FIG. 2.

FIG. 10 is a side elevational view of the areal pad of FIG. 9.

FIG. 11 is a frontal view of another embodiment of an areal pad associated with the knee brace of FIG. 2.

FIG. 12 is a frontal view of a further embodiment of an areal pad associated with the knee brace of FIG. 2.

DESCRIPTION OF PREFERRED EMBODIMENTS

Figure 1:
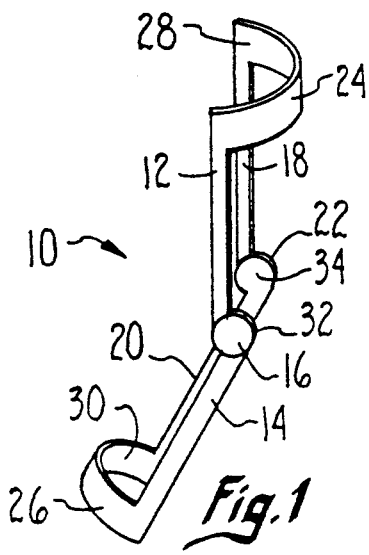
FIG. 1 is a perspective view of a knee brace having utility in the present invention.

Referring initially to FIG. 1, an orthopedic brace having utility in the present invention is shown and generally designated 10. The particular orthopedic brace 10, shown by way of example, is a knee brace of conventional design having a plurality of rigid structural components including medial upper and lower arms 12, 14, a medial hinge 16, lateral upper and lower arms 18, 20, a lateral hinge 22, an upper leg cuff 24, and a lower leg cuff 26. Upper and lower leg cuffs 24, 26 both have a similar curved shape providing them with concave inner faces 28 and 30, respectively, while medial and lateral hinges 16 and 22 have relatively flat inner faces 32 and 34, respectively.

Figure 2:
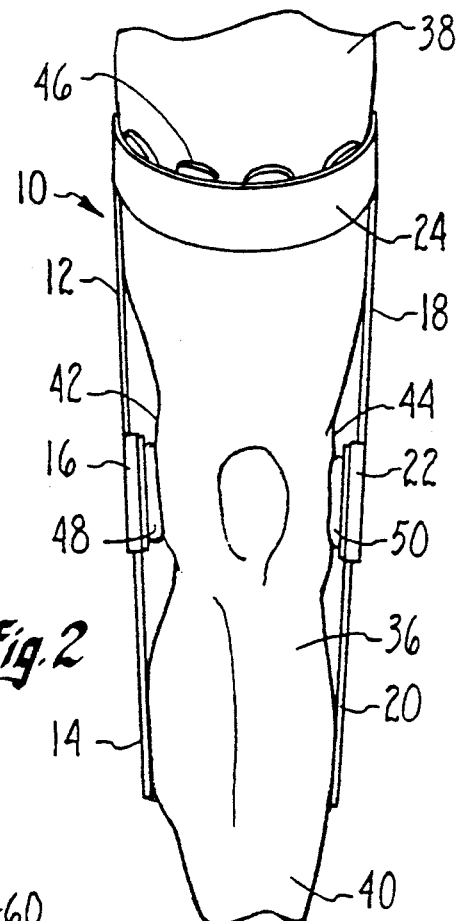
FIG. 2 is a frontal view of the knee brace of the present invention in place on the leg of a user.

Brace 10 is shown in FIG. 2 positioned on the leg 36 of a user. Inner face 28 of upper leg cuff 24 conformingly engages upper leg 38 and inner face 30 of lower leg cuff 26 (obscured from view in FIG. 2) conformingly engages lower leg 40, thereby supporting brace 10 against leg 36. Support of brace 10 against leg 36 is further provided by engagement of inner face 32 of medial hinge 16 with medial knee condyle 42 and engagement of inner face 34 of lateral hinge 22 with lateral knee condyle 44. Typically, a plurality of adjustable flexible straps (not shown) are also provided which loop through arms 12, 14, 18, 20 to further secure brace 10 to the leg 36 by increasing the compression force at the points of contact between brace 10 and the leg 36.

To enhance engagement of the rigid structural components of brace 10 with leg 36 while simultaneously promoting the comfort of the user, a plurality of pneumatic pads are additionally mounted on brace 10 in accordance with the present invention at the points of compression contact with the leg 36. In particular, an areal pad, shown here as cuff pad 46, is mounted on the inner face 28 of upper leg cuff 24 to rest in compression between the upper leg 38 and face 28 when cuff 24 engages the upper leg 38. Although not shown, a second areal pad substantially similar to cuff pad 46 is also mounted on the inner face 30 of lower leg cuff 26 to rest in compression between the lower leg 40 and face 30 when cuff 26 engages the lower leg 40.

A point pad, shown here as a medial condyle pad 48, is mounted on the inner face 32 of medial hinge 16 to rest in compression between the medial knee condyle 42 and face 32 when hinge 16 engages knee condyle 42. A second point pad, shown here as a lateral condyle pad 50, substantially identical to medial condyle pad 48 is mounted on the inner face 34 of lateral hinge 22 to rest in compression between the lateral knee condyle 44 and face 34 when hinge 22 engages knee condyle 44. Condyle pads 48 and 50 are described hereafter with reference to FIGS. 3-5.

Figure 3:
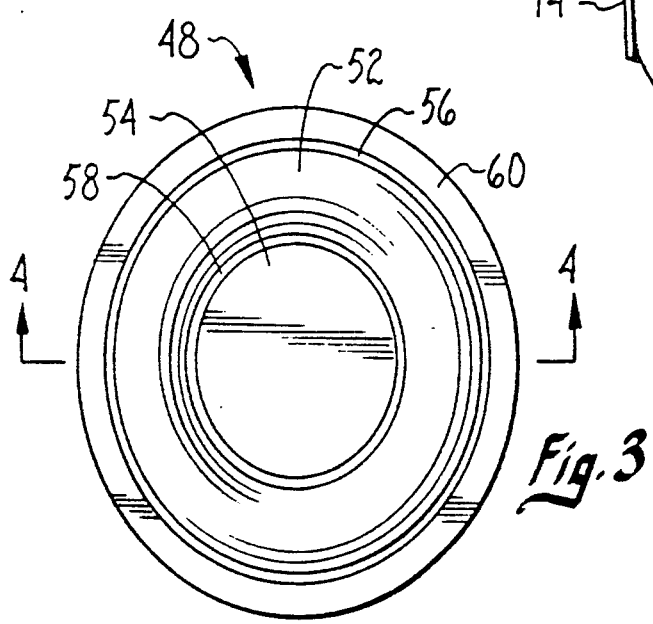
FIG. 3 is a frontal view of a point pad associated with the knee brace of FIG. 2.

Referring initially to FIG. 3, a preferred embodiment of condyle pad 48 is shown comprising a first or primary bladder 52, a second or secondary bladder 54, a first seam 56, a second seam 58, and a backing 60. First seam 56 continuously surrounds first bladder 52 following a closed-loop pathway, thereby defining the entire outer perimeter of the substantially toroidal shape of first bladder 52. Second seam 58 is positioned within first seam 56 concentric therewith. Like first seam 56, second seam 58 follows a continuous closed-loop pathway. Second seam 58 defines both the entire inner perimeter of first bladder 52 and the entire outer perimeter of second bladder 54. Accordingly, second bladder 54 lies in fluid isolation from first bladder 52 concentrically within the interior of toroidal-shaped first bladder 52. Backing 60 is provided as an elastic cushion, positioned behind and attached to both bladders 52 and 54.

Figure 4:
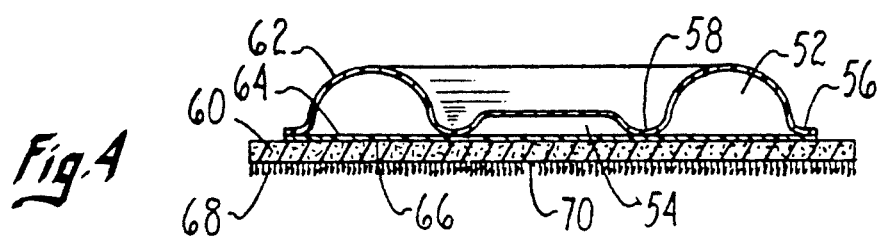
FIG. 4 is a cross-sectional view of the point pad of FIG. 3 as seen along line 4—4.

Details of the preferred construction of condyle pad 48 are described with reference to FIG. 4, wherein bladders 52 and 54 are shown to comprise two continuous sheets 62, 64 of a film material. The film material is a highly-flexible, elastically-collapsible, fluid-impervious material such as a plastic, e.g., polyurethane or polyvinyl chloride. Bladders 52 and 54 are constructed by thermoforming first sheet 62 in a hemi-toroidal shape and overlaying it atop flat second sheet 64. First seam 56 is then formed by joining sheets 62, 64 together along the continuous toroidal path of the outer perimeter using conventional means, such as high radio frequency (r.f.) welding.

Simultaneous with the formation of first seam 56, a predetermined volume of fluid is injected into the interior of first seam 56. Completion of first seam 56 substantially seals the interior to the external environment and maintains the injected fluid therein. The injected fluid is preferably a gas at ambient temperature, such as air, sulfur hexafluoride, or a mixture thereof. The injected gas most preferably has a substantially higher molecular weight than air to reduce long-term leakage of gas through the film by diffusion.

Construction of bladders 52, 54 is completed by the formation of second seam 58 which is concentric with first seam 56, and surrounded thereby. Second seam 58 is formed by joining sheets 62, 64 together around the continuous inner perimeter of the toroid using conventional means such as r.f. welding. Accordingly, formation of the first and second seams 56, 58 in sheets 62, 64 establishes bladders 52, 54 with first bladder 52 being inflated to a height substantially greater than the height of second bladder 54. In other words, the distance separating sheets 62, 64 within the first bladder 52 is substantially greater than the distance of separation within the second bladder 54.

Having constructed bladders 52, 54, construction of the pad 48 is completed by laminating backing 60 onto the backside 66 of second sheet 64. Although backing 60, like sheets 62, 64, is formed from an elastic material, the material of backing 60 is thicker and substantially less pliable than the film material of sheets 62, 64. Backing 60 is preferably formed from an elastomeric foam having a thickness of about ⅛ inches or more. Lamination of backing 60 onto backside 66 is readily accomplished by adhesion with a conventional glue.

Finally, pad 48 is provided with a fastener enabling removable fastening of backing 60 to the inner face 32 of medial hinge 16. A preferred fastener is a hook and loop fastener, commonly termed VELCRO, as shown in FIG. 4, wherein a cloth patch of the hook component 68 is laminated to the backside 70 of backing 60. A cloth patch of the loop component (not shown) is similarly laminated to inner face 32 opposite backside 70. It is understood that the positions of the hook and loop components can alternatively be reversed such that the hook component is laminated to inner face 32 and the loop component is laminated to backside 70.

FIG. 5 shows an alternate embodiment of a fastener for removably fastening backing 60a of pad 48a to inner face 32. The fastener of FIG. 5 comprises a fastener plate 72, a pair of screws 74a, 74b, a pair of internally threaded rivets 76a, 76b, and a padded screw cover 78. Screw holes 80a,b, 82a,b, 84a,b, and 86a,b are provided in medial hinge 16, backing 60a, second bladder 54a, and fastener plate 72, respectively. Fastener plate 72 is a rigid plate formed from a lightweight high-strength material, such as a rigid plastic or metal. Screw cover 78 is an elastic material such as used in the construction of backing 60 or 60a.

Pad 48a is assembled by inserting rivets 76a, 76b into screw holes 80a,b. Backing 60a, second bladder 54a, and fastener plate 72 are then stacked onto inner face 32 such that rivets 76a, 76b fit through screw holes 82a,b, 84a,b, and 86a,b. Screws 77a, 74b are then inserted into rivets 76a, 76b and threaded therein. Finally, screw cover 78 is press fitted over second bladder 54a and the heads of screws 74a, 74b to nest within the interior of the toroid formed by first bladder 52a. It is noted that, in addition to being in fluid isolation from first bladder 52a, second bladder 54a can, if desired, be maintained fluidtight despite the presence of screw holes 84a,b, by providing seams (not shown) of the type described above around the screw holes.

Although preferred embodiments of a condyle pad 48, 48a have been shown and described above, it is apparent that other embodiments of condyle pads, although not shown, are possible within the scope of the present invention. For example, the present invention further provides for an alternate embodiment of a condyle pad having only a single primary bladder similar in configuration to bladder 52 of FIG. 3. Unlike pad 48 of FIG. 3, however, a secondary bladder is excluded from the central opening of the toroidal-shaped bladder so that the opening is maintained as a void.

Further within the scope of the present invention, it is understood that the primary bladder of the point pad need not have a toroidal shape, but may have substantially any shape defining a closed-loop pathway that conforms to the perimeter of a skeletal protrusion and that provides an interior opening for receiving the apex of the protrusion. It is desirable that sufficient fluid be placed in the primary bladder to maintain the height of the primary bladder greater than the height of the protrusion received therein during use of the brace to prevent substantial compressive contact of the bony protrusion with the rigid structural components of the brace to which the pad is mounted.

Alternative means for producing the point pad of the present invention are also provided within the scope of the invention. For example, the three dimensional shape of the primary bladder can be achieved exclusively by inflation of the bladder, rather than by providing a preformed shape to the bladder via thermoforming of the bladder's exterior film material. Additionally, the primary bladder can be formed from a single sheet of film material, rather than two sheets as disclosed above, by joining the edges of a single sheet together and welding the resulting joint, thus, forming a bladder sealed at the weld or welds. In other production alternatives, the primary bladder may be formed by blow molding or other conventional molding methods available to one skilled in the art.

Referring to FIGS. 6, 7, and 8, further alternatives to the point pad as used on the brace of the present invention are shown, and specifically alternate configurations are shown to the primary bladder of a condyle pad. Referring initially to FIG. 6, a primary bladder 88 is shown that is substantially toroidal-shaped in the manner of bladder 52 of FIG. 3, but is divided into a plurality of interconnected, but fluid-isolated, cells 90a, 90b, 90c, 90d by intervening seams 92a, 92b, 92c, 92d formed therebetween.

Referring next to FIG. 7, a primary bladder 94 is shown that is substantially toroidal-shaped in the manner of bladder 52 of FIG. 3, but has a relatively limited open 96 in its pathway. Finally, referring to FIG. 8, a primary bladder 98 is shown that is substantially toroidal-shaped in the manner of bladder 52 of FIG. 3, although somewhat more oval. Bladder 98 is further provided with a central flowpath segment 100 having narrowed channels 102a, 102b that penetrate seam 104 to enable fluid communication between the main toroidal body 106 of bladder 98 and segment 100. In operation segment 100 is substantially deflated due to compression against the condyle with the fluid contained in segment 100 being displaced to main body 106 through channels 102a, 102b.

Despite variations in the primary bladder configurations shown in FIGS. 3, 6, 7 and 8, all of these embodiments are characterized as having primary bladders defining a "substantially closed-loop pathway," as the term is used herein, with an interior opening.

A brace having one or more areal pads embodied by the present invention is now described in greater detail with reference to FIGS. 9 and 10, wherein the configuration of cuff pad 46 is shown. Cuff pad 46 comprises a plurality of first bladders 108a, 108b, 108c and 108d and a plurality of second bladders 110a, 110b, 110c, 110d, and 110e positioned between each successive first bladder 108. First seams 112a, 112b are substantially horizontal seams which define portions of the outer perimeters of both first and second bladders 108 and 110. Likewise, second seams 114a, 114b, 114c, 114d, 114e, 114f, 114g, 114h, 114i, 114j are substantially vertical seams which define portions of the outer perimeters of both first and second bladders 108 and 110.

Holes 116 to receive fasteners, such as screws or tabs (not shown), are also provided through second bladders 110 in a manner similar to condyle pad 48a of FIG. 5. Alternatively, a hook and loop fastener can be provided on the backside of cuff pad 46 in a manner similar to condyle pad 48 of FIG. 4. FIG. 10 indicates that cuff pad 46 has no cushion backing, although such a backing can optionally be provided. In other respects, the construction of cuff pad 46 is substantially similar to that of condyle pad 48 shown in FIG. 4.

Cuff pad 46 is preferably formed from two sheets 118, 120 of flexible film material. First sheet 118 is thermoformed in a repeating pattern of ridges according to the configuration of first and second bladders 108, 110 and second sheet 120 is maintained flat. Sheets 118, 120 are joined together at first and second seams 112, 114 such that first bladders 108 are in fluid isolation from the outside environment and from second bladders 110. First bladders 108 have a height substantially greater than the height of each second bladder 110, the second bladder 110 being preferably uninflated or relatively underinflated such that second bladders 110 are substantially more flexible than first bladders 108.

When cuff pad 46 is positioned between upper leg cuff 24 and upper leg 38 as shown in FIG. 2, it enhances the support function of the cuff 24 as well as enhancing user comfort. Compression of pad 46 against upper leg 38 spreads flexible first bladders 108 across a large contact surface providing a close grip on leg 38. A cloth covering (not shown) can also be provided over first bladders 108 which increases the friction between the pad 46 and the upper leg 38 and further improves the grip thereon. By positioning cuff pad 46 at the surface of engagement between cuff 24 and upper leg 38, the load of cuff 24 is more evenly distributed across the area of the upper leg 38. Consequently, user comfort is increased by eliminating point loads on the leg 36.

Alternative methods for producing cuff pad 46 similar to those alternative methods described above with respect to production of the condyle pad are also within the scope of the present invention. Likewise within the scope of the present invention are other configurations of the areal pad than that shown in FIGS. 9 and 10. Areal pads within the scope of the present invention are broadly characterized as having a series of interconnected gas-inflated chambers maintained in fluid isolation from one another by seams providing articulation of the pad.

Thus, for example, referring to FIG. 11, an alternate embodiment of an areal pad, shown here as cuff pad 122, is sized to cover substantially the entire inner face of a cuff in the same manner as cuff pad 46 shown in FIG. 2. However, rather than having multiple bladders, cuff pad 122 has only one bladder 124 which is divided by a plurality of substantially vertical seams 126a, 126b, 126c, and 126d to form a plurality of adjacent cells 128a, 128b, 128c, 128d, and 128e in bladder 124 which are in fluid isolation from one another. Seams 126 are substantially more flexible than inflated cells 128, and as such provide articulation of pad 122 in a similar manner to pad 46 as shown in FIG. 2.

It is noted that the term "chamber", as defined herein, refers to any containment in fluid isolation and is, thus, inclusive of the terms "bladder" and "cell" as used herein. It is further noted that pad 122 is provided with a slight curve in its horizontal orientation and its vertical seams 126 have a slight inward angle to enable better conformance of the pad with curvature of the leg. This conformance enhancing configuration can likewise be applied to cuff pad 46.

A further alternate embodiment of an areal pad within the scope of the present invention is described with reference to FIG. 12. A cuff pad is shown therein and designated 130. Cuff pad 130 has a similar configuration to cuff pad 122 of FIG. 11. However, cuff pad 130 comprises a single bladder 132 divided into a plurality of adjacent fluid-communicating segments 134a, 134b, 134c, 134d, and 134e. Segments 134 are separated by seams 136a, 136b, 136c, and 136d, but fluid communication is provided therethrough by narrow flow channels 138a, 138b, 138c, and 138d. Accordingly, seams 136 provide for articulation of pad 130 having a segmented single chamber construction.

In sum, areal pads, and particularly cuff pads, have been shown to improve the fit of the brace on the user while enhancing user comfort. Point pads, and particularly condyle pads, used on a brace in conjunction with the areal pads or by themselves advantageously provide additional areas of brace support against the body of the user which are both highly secure and comfortable to the user. As noted above, the point pad is sized and configured such that the primary bladder surrounds and grips the perimeters of the desired skeletal protrusion while the bony apex of the protrusion rests in the depression formed by the interior opening of the pad. Accordingly, the point pad, and specifically a condyle pad, provides a highly secure longitudinal, transverse and medial/lateral support for the brace when the pad is properly positioned on the leg without causing substantial discomfort to the user.

While the particular orthopedic braces having pneumatic pads as herein shown and disclosed in detail are fully capable of obtaining the objects and providing the advantages hereinbefore stated, it is to be understood that these braces and associated pads are merely illustrative of the presently preferred embodiments of the invention and that other embodiments are possible within the scope of the present invention.

I claim:

1. An orthopedic brace positionable on the body of a user comprising:
   a rigid hinge surface joining two rigid arms, said hinge surface positionable opposite a knee condyle of the user and adaptable to apply pressure thereto;
   a first sheet of an elastically deformable film positionable between said surface and the body of the user;
   a second sheet of an elastically deformable film positionable between said first sheet and the body of the user;
   a first seam sealingly joining said second sheet to said first sheet, thereby defining at least a portion of an outer perimeter of a first substantially fluidtight bladder between said first and second sheets, wherein said first bladder is formed substantially in the shape of a toroid;
   a second seam sealingly joining said second sheet to said first sheet, thereby defining at least a portion of an outer perimeter of a second bladder between said first and second sheets, said second bladder in fluid isolation from said first bladder;
   a volume of fluid contained within said first bladder, said volume of fluid sufficient to provide said first bladder with a height greater than the height of said second bladder.

2. An orthopedic brace as recited in claim 1 further comprising means for connecting said first sheet to said rigid surface.

3. An orthopedic brace as recited in claim 1 further comprising an elastic cushion attached to said first sheet between said first sheet and said surface, wherein said cushion is substantially thicker than said first sheet.

4. An orthopedic brace as recited in claim 3 wherein said elastic cushion is relatively less elastic than said first sheet.

5. An orthopedic brace as recited in claim 3 further comprising means for connecting said first sheet to said rigid surface.

6. An orthopedic brace as recited in claim 5 wherein said connecting means is a hook and loop fastener comprising a hook component and a loop component, and further wherein one component of said hook and loop fastener is attached to said elastic cushion and the other component is attached to aid rigid surface.

7. An orthopedic brace as recited in claim 1 wherein said first bladder is adaptable in size to circumscribe the knee condyle.

8. An orthopedic brace as recited in claim 7 wherein said second bladder is positionable opposite the knee condyle.

9. A pad mountable on an orthopedic brace to support the brace against a user's body when positioned thereon, said pad comprising:
- a first sheet of an elastically deformable film having two sides;
- a second sheet of an elastically deformable film positioned on the first side of said first sheet;
- means for connecting said first sheet to the brace;
- a first seam sealingly joining said second sheet to said first sheet, thereby defining at least a portion of an outer perimeter of a first substantially fluidtight bladder between said first and second sheets;
- a second seam sealingly joining second sheet to said first sheet, thereby defining at least a portion of an outer perimeter of a second bladder between said first and second sheets, said second bladder in fluid isolation from said first bladder, wherein said first bladder is formed in the shape of a toroid and said second bladder is concentric with said toroid;
- a volume of fluid contained within said first bladder, said volume of fluid sufficient to provide said first bladder with a height greater than the height of said second bladder.

10. A pad mountable on an orthopedic brace as recited in claim 9 further comprising an elastic cushion attached to the second side of said first sheet, wherein said cushion is substantially thicker than said first sheet.

11. A pad mountable on an orthopedic brace as recited in claim 9 wherein said connecting means is a hook and loop fastener comprising a hook component and a loop component, and further wherein one component of said hook and loop fastener is attached to said elastic cushion.

12. A pad mountable on an orthopedic brace as recited in claim 9 wherein said first bladder is adaptable in size to surround the perimeter of a knee condyle of the user and said second bladder is positionable opposite the knee condyle.

13. A pad mountable on an orthopedic brace as recited in claim 9 wherein said fluid is a gas having a substantially higher molecular weight than air.

14. An orthopedic brace positionable on the body of a user comprising:
- a rigid hinge surface joining two rigid arms, said hinge surface positionable opposite a condyle on the body of the user and adaptable to apply pressure thereto;
- a bladder formed substantially in the shape of a toroid and positionable between said rigid surface and the condyle, said bladder having a fluid sealably contained therein and defining a substantially closed-loop pathway with an interior opening, wherein said pathway is adaptable in size to circumscribe the condyle and said opening is adaptable in size to receive a bony protrusion of the condyle, and further to prevent substantial contact between said rigid surface and said bony protrusion as said surface applies pressure to the body.

15. An orthopedic brace as recited in claim 14 further comprising means for connecting said bladder to said rigid surface.

16. An orthopedic brace as recited in claim 15 wherein said connecting means is a hook and loop fastener comprising a hook component and a loop component.

17. An orthopedic brace as recited in claim 14 further comprising a secondary bladder within said opening, wherein said secondary bladder has a height substantially less than the height of said bladder.

18. An orthopedic brace as recited in claim 14 wherein said bladder has a flowpath segment positioned within said opening, wherein said flowpath segment is in fluid communication with said bladder.

* * * * *